United States Patent
Ono et al.

(10) Patent No.: US 6,826,735 B2
(45) Date of Patent: Nov. 30, 2004

(54) INSPECTION DATA ANALYSIS PROGRAM, DEFECT INSPECTION APPARATUS, DEFECT INSPECTION SYSTEM AND METHOD FOR SEMICONDUCTOR DEVICE

(75) Inventors: Makoto Ono, Yokohama (JP); Hisafumi Iwata, Hayama (JP); Kanako Harada, Yokohama (JP)

(73) Assignee: Hitachi, Ltd., Tokyo (JP)

(*) Notice: Subject to any disclaimer, the term of this patent is extended or adjusted under 35 U.S.C. 154(b) by 49 days.

(21) Appl. No.: 10/196,146

(22) Filed: Jul. 17, 2002

(65) Prior Publication Data

US 2003/0058436 A1 Mar. 27, 2003

(30) Foreign Application Priority Data

Sep. 26, 2001 (JP) ........................................ 2001-292781

(51) Int. Cl.[7] .............................................. G06F 17/50
(52) U.S. Cl. ............................................. 716/4; 716/19
(58) Field of Search ................................ 716/4, 19–21; 700/108–110; 382/141–145, 149, 115; 430/5

(56) References Cited

U.S. PATENT DOCUMENTS

| 4,803,734 | A | * | 2/1989 | Onishi et al. ................ 382/115 |
| 5,801,965 | A |   | 9/1998 | Takagi et al. |
| 6,625,800 | B1 | * | 9/2003 | Qian et al. ..................... 716/19 |
| 2001/0048761 | A1 | * | 12/2001 | Hamamatsu et al. ........ 382/149 |
| 2002/0052053 | A1 | * | 5/2002 | Ono et al. ..................... 438/12 |
| 2002/0057831 | A1 | * | 5/2002 | Hiroi et al. .................. 382/149 |
| 2002/0098421 | A1 | * | 7/2002 | Hasegawa et al. ............. 430/5 |

FOREIGN PATENT DOCUMENTS

| JP | A-10-115594 | 5/1998 |
| JP | A-10-209230 | 8/1998 |
| JP | A-2000-223385 | 8/2000 |

* cited by examiner

*Primary Examiner*—Vuthe Siek
(74) *Attorney, Agent, or Firm*—Antonelli, Terry, Stout & Kraus, LLP

(57) ABSTRACT

Inspection data output from an inspection apparatus is read, the inspection data containing at least one information piece of coordinate value information and size information of a particle or a pattern defect of an inspected object, and drawing data of a product of the inspected object is read. Information is extracted which is representative of a relation between at least one information piece of coordinated value information and size information of the particle or pattern defect of the inspected object in the read inspection data and the read drawing data input at said drawing data input step. The extracted information is compared with determination criterion information registered beforehand and it is determined whether each particle or pattern defect of the inspected object in the inspection data is a detection error or not.

17 Claims, 14 Drawing Sheets

```
PRODUCT NAME  ASIC3200
LOT NUMBER  L001
WAFER NUMBER  10
INSPECTION PROCESS  METAL1
DEFECT NUMBER, CHIP COLUMN, CHIP ROW,    X,        Y,       SIZE
       1,            1,         1,    5000000,  7000000,   1000
       2,            5,         1,    2500000,  8900000,   3500
       3,            4,         2,    4700000,  6900000,   1200
       4,            5,         3,    8000000,  8200000,   5600
       5,            6,         5,    5200000,  7800000,   1100
       6,            3,         5,    7100000,  3200000,  12300
       7,            3,         7,    8700000,  9000000,   7200
       8,            2,         6,    7700000,  3800000,   1500
       9,            0,         4,    8300000,  4500000,   8500
```
— 31

```xml
<?xml version="1.0"?>
<OBJECT>
<PRODUCT>ASIC3200</PRODUCT>
<LOT>L001</LOT>
<WAFER>10</WAFER>
<LAYER>METAL1</LAYER>
<DETECTION>
    <DIE_X>1</DIE_X>
    <DIE_Y>1</DIE_Y>
    <COORDINATE_X>5000000</COORDINATE_X>
    <COORDINATE_Y>7000000</COORDINATE_Y>
    <SIZE>1000</SIZE>
    <THRESHOLD_FOR_NEIGHBORS>200000</THRESHOLD_FOR_NEIGHBORS>
    <THE_NUMBER_OF_NEIGHBORS>2</THE_NUMBER_OF_NEIGHBORS>
</DETECTION>
<LAYOUT>
    <CIRCUIT_BLOCK>
        <BLOCK_NAME>ROOT</BLOCK_NAME>
        <LENGTH_LEFT>5000000</LENGTH_LEFT>
        <LENGTH_RIGHT>5000000</LENGTH_RIGHT>
        <LENGTH_UP>3000000</LENGTH_UP>
        <LENGTH_DOWN>7000000</LENGTH_DOWN>
    </CIRCUIT_BLOCK>
    <CIRCUIT_BLOCK>
        <BLOCK_NAME>B2</BLOCK_NAME>
        <LENGTH_LEFT>1000000</LENGTH_LEFT>
        <LENGTH_RIGHT>5000000</LENGTH_RIGHT>
        <LENGTH_UP>3000000</LENGTH_UP>
        <LENGTH_DOWN>4000000</LENGTH_DOWN>
    </CIRCUIT_BLOCK>
```

FIG. 12

```
<CIRCUIT_PATTERN>
    <BLOCK_NAME>B2</BLOCK_NAME>
    <RANGE_SIZE_X>10000</RANGE_SIZE_X>
    <RANGE_SIZE_Y>10000</RANGE_SIZE_Y>
    <RESOLUTION_X>20</RESOLUTION_X>
    <RESOLUTION_Y>20</RESOLUTION_Y>
    <BITMAP>
        0,1,0,1,1,1,1,0,1,1,1,1,1,1,1,1,0,1,1
        0,1,0,1,1,1,1,0,1,1,1,1,1,1,1,1,0,1,1
        1,1,0,0,0,0,0,0,1,1,0,0,0,0,0,0,0,1,1
        1,1,0,1,1,0,0,0,1,1,1,1,0,0,0,0,0,1,1
        1,1,0,1,1,0,0,0,1,1,1,1,0,0,0,0,0,1,1
        0,0,0,1,1,0,0,0,1,1,0,1,0,0,0,0,0,1,1
        0,0,0,1,1,0,0,0,1,1,0,1,0,0,0,0,0,1,1
        0,0,0,1,1,0,0,0,1,1,0,1,0,0,0,0,0,1,1
        0,0,0,1,1,0,0,0,1,1,0,1,0,0,0,0,0,1,1
        0,0,0,1,1,0,0,0,1,1,0,1,0,0,0,0,0,1,1
        0,1,1,1,1,0,0,0,1,1,0,1,0,1,1,0,1,0,1,1
        0,1,1,1,1,0,0,0,1,1,0,1,0,1,1,1,1,0,1,1
        1,1,0,0,0,0,0,0,1,1,0,1,0,1,1,1,1,0,1,1
        1,1,0,1,1,0,0,0,1,1,0,1,0,1,1,0,1,0,1,1
        1,1,0,1,1,0,0,0,1,1,0,1,0,1,1,0,1,0,1,1
        0,0,0,1,1,0,1,0,1,1,0,1,0,1,1,1,1,0,1,1
        0,0,0,1,1,1,1,0,1,1,0,1,0,1,1,1,1,0,1,1
        0,0,0,1,1,1,1,0,1,1,0,1,0,0,0,0,0,0,1,1
        1,1,1,1,1,0,1,0,1,1,0,1,0,1,1,0,1,1,1,1
        1,1,1,1,0,0,1,0,1,1,0,1,0,1,1,0,1,1,1,0
    </BITMAP>
</CIRCUIT_PATTERN>
</LAYOUT>
</OBJECT>
```

FIG. 13

```xml
<?xml version="1.0"?>
<RULE>
<PRODUCT>ASIC3*</PRODUCT>
<LAYER>METAL1</LAYER>
<LAYOUT>
    <CIRCUIT_PATTERN>
        <RANGE_SIZE_X>10000</RANGE_SIZE_X>
        <RANGE_SIZE_Y>10000</RANGE_SIZE_Y>
        <RESOLUTION_X>20</RESOLUTION_X>
        <RESOLUTION_Y>20</RESOLUTION_Y>
        <BITMAP>
            0,0,1,0,1,1,1,1,0,1,1,1,1,1,1,1,1,1,0,1
            0,0,1,0,1,1,1,1,0,1,1,1,1,1,1,1,1,1,0,1
            1,1,1,0,0,0,0,0,0,1,1,0,0,0,0,0,0,0,0,1
            1,1,1,0,1,1,0,0,0,1,1,1,1,0,0,0,0,0,0,1
            1,1,1,0,1,1,0,0,0,1,1,1,1,0,0,0,0,0,0,1
            0,0,0,0,1,1,0,0,0,1,1,0,1,0,0,0,0,0,0,1
            0,0,0,0,1,1,0,0,0,1,1,0,1,0,0,0,0,0,0,1
            0,0,0,0,1,1,0,0,0,1,1,0,1,0,0,0,0,0,0,1
            0,0,0,0,1,1,0,0,0,1,1,0,1,0,0,0,0,0,0,1
            0,0,0,0,1,1,0,0,0,1,1,0,1,0,0,0,0,0,0,1
            0,0,1,1,1,1,0,0,0,1,1,0,1,0,1,1,0,1,0,1
            0,0,1,1,1,1,0,0,0,1,1,0,1,0,1,1,1,1,0,1
            1,1,1,0,0,0,0,0,0,1,1,0,1,0,1,1,1,1,0,1
            1,1,1,0,1,1,0,0,0,1,1,0,1,0,1,1,0,1,0,1
            1,1,1,0,1,1,0,0,0,1,1,0,1,0,1,1,0,1,0,1
            0,0,0,0,1,1,0,1,0,1,1,0,1,0,1,1,1,1,0,1
            0,0,0,0,1,1,1,1,0,1,1,0,1,0,1,1,1,1,0,1
            0,0,0,0,1,1,1,1,0,1,1,0,1,0,0,0,0,0,0,1
            1,1,1,1,1,1,0,1,0,1,1,0,1,0,1,1,0,1,1,1
            1,1,1,1,1,0,0,1,0,1,1,0,1,0,1,1,0,1,1,1
        </BITMAP>
        <MATCHING_RANGE>2</MATCHING_RANGE>
        <MATCHING_RATE>0.9-1.0</MATCHING_RATE>
    </CIRCUIT_PATTERN>
</LAYOUT>
</RULE>
```

FIG. 14

```xml
<?xml version="1.0"?>
<RULE>
<PRODUCT>ASIC3*</PRODUCT>
<LAYER>METAL1</LAYER>
<DETECTION>
      <SIZE>0-2000</SIZE>
      <THRESHOLD_FOR_NEIGHBORS>200000</THRESHOLD_FOR_NEIGHBORS>
      <THE_NUMBER_OF_NEIGHBORS>2</THE_NUMBER_OF_NEIGHBORS>
</DETECTION>
<LAYOUT>
      <CIRCUIT_BLOCK>
            <BLOCK_NAME>B2</BLOCK_NAME>
            <LENGTH_LEFT>3000000+-20000</LENGTH_LEFT>
            <LENGTH_UP>1000000+-10000</LENGTH_UP>
      </CIRCUIT_BLOCK>
</LAYOUT>
</RULE>
```

FIG. 15

```
PRODUCT NAME  ASIC3200
LOT NUMBER  L001
WAFER NUMBER  10
INSPECTION PROCESS  METAL1                              DETECTION
DEFECT NUMBER, CHIP COLUMN, CHIP ROW,    X,        Y,     SIZE  ERROR
             1,           1,         1,  5000000,  7000000, 1000    1
             2,           5,         1,  2500000,  8900000, 3500    0
             3,           4,         2,  4700000,  6900000, 1200    1
             4,           5,         3,  8000000,  8200000, 5600    0
             5,           6,         5,  5200000,  7800000, 1100    0
             6,           3,         5,  7100000,  3200000, 12300   0
             7,           3,         7,  8700000,  9000000, 7200    0
             8,           2,         6,  7700000,  3800000, 1500    0
             9,           0,         4,  8300000,  4500000, 8500    0
```
33

INSPECTION DATA ANALYSIS PROGRAM, DEFECT INSPECTION APPARATUS, DEFECT INSPECTION SYSTEM AND METHOD FOR SEMICONDUCTOR DEVICE

BACKGROUND OF THE INVENTION

The present invention relates to a defect inspection apparatus and system to be used in manufacture processes of an electronic device such as a semiconductor integrated circuit, and to a defect inspection program to be executed in the defect inspection apparatus and system.

Related art will be described by taking manufacture of a semiconductor integrated circuit as an example. Processes of manufacturing a semiconductor integrated circuit are generally classified into a front-end process and a back-end process. In the former process, a plurality of chips (products) with multiple layers such as a circuit pattern are formed on a silicon wafer. In the latter process, the silicon wafer is separated into each chip to complete each product. Most of failures during manufacture occur in the long term front-end process including fine patterning. Improvement on the yield of the front-end process is important for low cost production. The yield of the front-end process is a non-defective product factor, i.e., a ratio of non-defective chips to all chips of a wafer, to be determined by the final electrical inspection of the front-end process.

Failures of the front-end process are mainly classified into operational failures and parametric failures. The functional failure is the failure that a circuit does not operate normally because of breakage or short circuit of a circuit pattern mainly caused by particles or pattern defects (hereinafter collectively called defects) generated during manufacture. The parametric failure is the failure that an operation speed of a transistor does not satisfy the design specification because of fine process variations in worked sizes, oxide film thicknesses and the like.

In order to detect particles and pattern defects which cause the functional failure, a defect inspection tool or apparatus such as a dark-field inspection tool or apparatus and a bright-field inspection tool or apparatus has been used at a front-end manufacture line. Generally, the dark-field inspection tool obliquely applies a laser beam to a wafer from an upper position and detects scattered light of the laser beam. The bright-field inspection tool picks up an image of a circuit pattern on a wafer and compares it with a normal pattern image to detect a difference between the normal pattern and abnormal pattern. Depending upon detectors, there are bright-field inspection tools of an optical type and of an electron beam type.

In general manufacture lines, defect data detected with a defect inspection tool is managed in the following manners to improve the manufacture yield.

(1) As described in JP-A-10-115594 and etc., defect data is managed by using a general quality management approach such as a time sequential change in the number of defects and a correlation between the number of defects and a manufacture yield.

(2) As described in JP-A-2000-223385 and etc., defect data is utilized for the analysis of a defect source by comparing the defect data and electrical test results on the basis of coordinate positions in a wafer plane and calculating an influence degree of defects upon a lowered manufacture yield.

(3) As described in JP-A-10-209230 and etc., defect data is utilized for the analysis of a defect source by analyzing the coordinate distribution of defect data in a wafer plane.

(4) As described U.S. Pat. No. 5,801,965 and etc., defect data is utilized for the analysis of a defect source by selecting several defect data pieces from the defect data and picking up each image of these defect data pieces with an image pickup apparatus called a defect review tool or apparatus.

SUMMARY OF THE INVENTION

The above-described analysis of defect data is performed on the assumption that all data detected with the defect inspection tool necessarily pertains to actual defects. However, data output from the defect inspection tool includes data pieces relevant to the electrical failure and many other data pieces irrelevant to the electrical failure called nuisance detection or detection error (also called quasi defects). Detection errors include some color variation of a circuit pattern, projections on a circuit pattern called grains, excessive reflection of light applied to a circuit pattern, a fine change in a line width of a circuit pattern and the like, which are neither actual particles nor pattern defects.

Recent semiconductor integrated circuits are becoming finer and finer and even a fine defect may cause a functional failure. A defect inspection tool is required to detect a fine defect, and often used at the ultimate point of the tool specification. In such a case, detection errors are likely to be output.

Such data which contains detection errors may cause an erroneous determination. For example, in the above-described document (1), even if a time sequential change in the number of defects increases, it may be merely an increase in the number of detection errors and the number of actual defects does not increase. In such a case, managing a time sequential change in the number of defects at a manufacture line is meaningless.

Also in the above-described document (4), even if an image of the data containing detection errors is picked up with a defect review tool, this image does not contain the defect to be dealt with and time is wasted.

A conventional method of removing such detection errors is described in JP-A-5-47887. With this method, it is assumed that defects repetitively detected at the same positions of LSI chips on a wafer are detection errors which are excluded from analysis. However, with this method, it is difficult to remove all detection errors.

It is an object of the present invention to provide a defect inspection apparatus and system and a defect inspection computer program capable of solving the problems associated with prior art.

It is another object of the invention to provide a defect inspection apparatus and system and a defect inspection computer program capable of efficiently and effectively detecting detection errors contained in an output of the defect inspection apparatus to exclude them from inspection data.

The present inventors have checked the occurrence positions of detection errors by using past inspection data.

FIG. 6 shows an example of a distribution of positions in an LSI chip from which a defect inspection apparatus output detection errors. In FIG. 6, data of detection errors detected with a defect inspection apparatus is plotted in a schematic LSI chip circuit layout (drawing information of a circuit pattern) 52. A solid black circle represents each detection error. Rectangular frames B1 to B4 represent circuit blocks 1 to 4. A circuit block is a unit which processes an individual function of LSI, such as an input/output block, an A/D converter block, a memory block and a processor block. Each circuit block is constituted of a collection of small circuit blocks. The minimum unit of the circuit block is generally a combinational circuit or a sequential circuit. It has been found from FIG. 6 that the occurrence positions of detection errors are dependent upon the circuit layout such as a boarder area between circuit blocks (e.g., 71a, 71b and 71c in FIG. 6), a peripheral area of a circuit block (e.g., 72a, 72b and 72c) and an inner area of a particular circuit block (e.g., 73a, 73b, 73c, 74a and 74b). It has also been found from the position distribution in an LSI chip that many detection errors do not exist singularly but they exist adjacent to each other.

The inventors have considered from these findings that detection errors can be selected from an output of a defect inspection apparatus and excluded from defect data by storing a relation between detection errors obtained from past inspection data and a circuit layout (drawing information of a circuit pattern) in a detection error database, comparing data newly output from the defect inspection apparatus with information in the detection error database, and determining the data matching the database information as a detection error.

According to one aspect of the present invention, an inspection data analyzing method of determining a detection error from output data of an inspection apparatus which detects a particle or a pattern defect of an inspected object, includes: an inspection data input step of reading inspection data output from the inspection apparatus, the inspection data containing at least one information piece of coordinate value information and size information of the particle or pattern defect of the inspected object; a drawing data input step of reading drawing data of a product of the inspected object; an information extracting step of extracting information representative of a relation between at least one information piece of coordinated value information and size information of the particle or pattern defect of the inspected object in the inspection data input at the inspection data input step, and the drawing data input at the drawing data input step; and a detection error determining step of comparing the information extracted at the information extracting step with determination criterion information registered beforehand and determining whether each particle or pattern defect of the inspected object in the inspection data is a detection error or not.

According to an embodiment of the invention, the determination criterion information is past inspection data of detection errors.

According to an embodiment of the invention, the determination criterion information is data representative of occurrence positions of past detection errors in a circuit block in the drawing data.

According to an embodiment of the invention, the drawing data to be read is circuit layout data generated by computer-aided design.

According to an embodiment of the invention, the extracted information includes coordinate value information of each particle or pattern defect of the inspected object in the inspection data in a circuit block corresponding to the drawing data.

According to the invention constructed as above, by using the past detection error data and the circuit layout information corresponding to the detection error data, the detection error database is created. It is therefore possible to efficiently find a detection error from inspection data newly output from the defect inspection apparatus. By utilizing the inspection data excluding detection errors for the defect analysis, the manufacture yield of electronic devices typically semiconductor integrated circuits can be improved effectively.

Other objects, features and advantages of the invention will become apparent from the following description of the embodiments of the invention taken in conjunction with the accompanying drawings.

BRIEF DESCRIPTION OF THE DRAWINGS

FIG. 10 shows an example of bit map data of a circuit pattern.

FIG. 11 shows an example of feature parameter data of the detection error candidate.

FIG. 12 shows an example of feature parameter data of the detection error candidate.

FIG. 13 shows an example of feature parameter data in a detection error database.

FIG. 14 shows an example of feature parameter data in a detection error database.

FIG. 15 shows an example of inspection data with detection error determination information.

DETAILED DESCRIPTION OF THE EMBODIMENTS

Embodiments of the invention will be described in detail with reference to the accompanying drawings.

Figure 1:
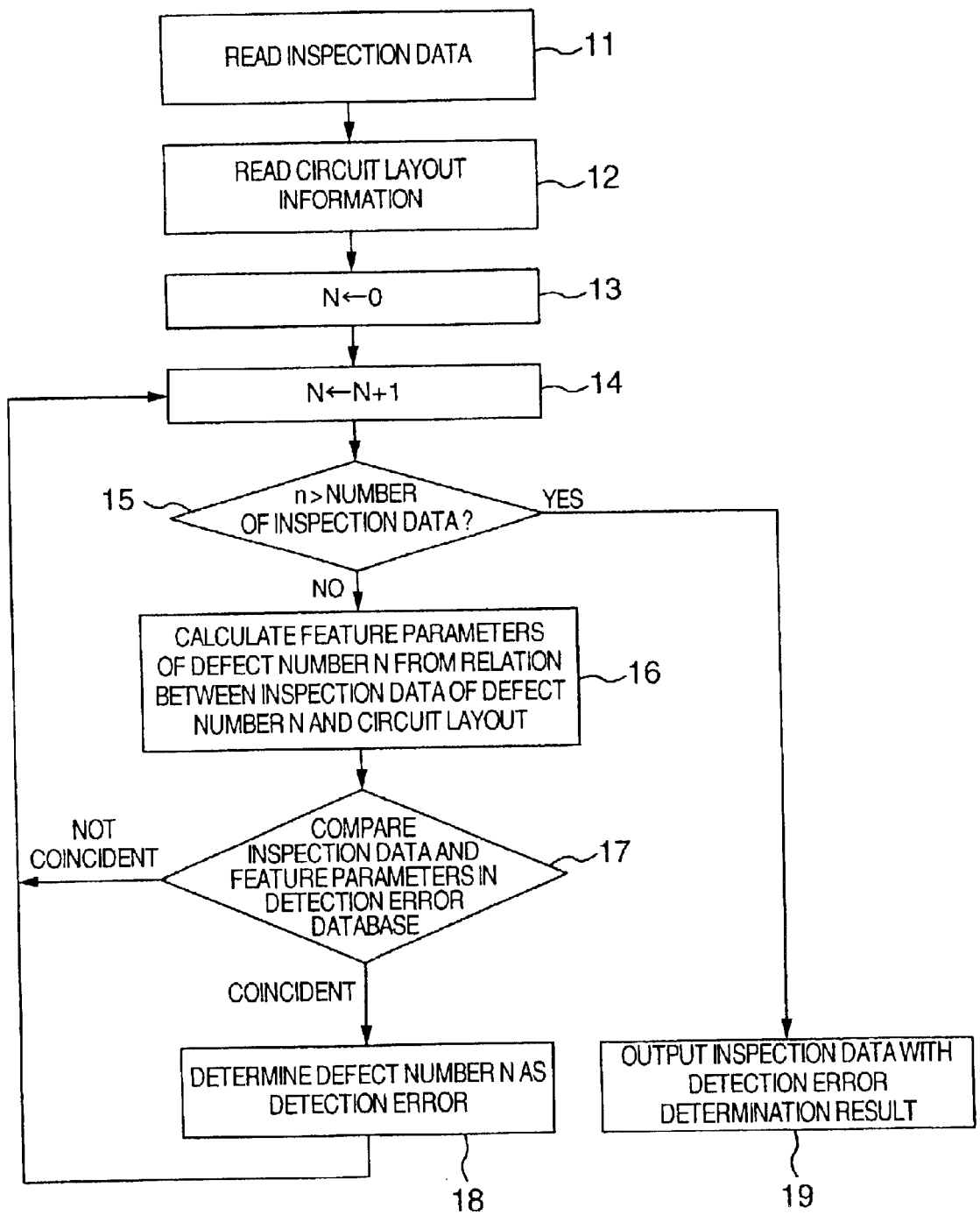
FIG. 1 is a flow chart illustrating an example of a detection error determining process according to an embodiment of the invention.

FIG. 1 is a flow chart illustrating an example of a program embodying the invention. First, at Step 11 inspection data output from a defect inspection apparatus is read, and at Step 12 circuit layout information of a product to be inspected is read. Next, at Step 13 "0" is input to a variable N. At Step 14 the value of the variable N is incremented by "1". At Step 15 if the value of the variable N is larger than the number of inspection data pieces read at Step 11, it is determined that all inspection data was subjected to a detection error determination, and the flow skips to Step 19. If the number of the variable N is equal to or smaller than the number of inspection data pieces, the flow advances to Step 16. At Step 16 information (feature parameters) of a defect having a defect number N is extracted from the relation between the inspection data having the detect number N and the circuit layout. The details of a feature parameter calculation method and the like will be later given. At Step 17 the inspection data having the defect number N is compared with the detection error feature parameters already registered in a detection error database, and if the inspection data and feature parameters match each other, the flow advances to Step 18, whereas if they do not match, the flow returns to Step 14. At Step 18 it is determined that the defect number N corresponds to a detection error, and a column of the defect number N of the inspection data is marked. At Step 19 the inspection data read at Step 11 and containing data determined as a detection error is output to thereafter complete the execution of the program.

Figures 2, 3:
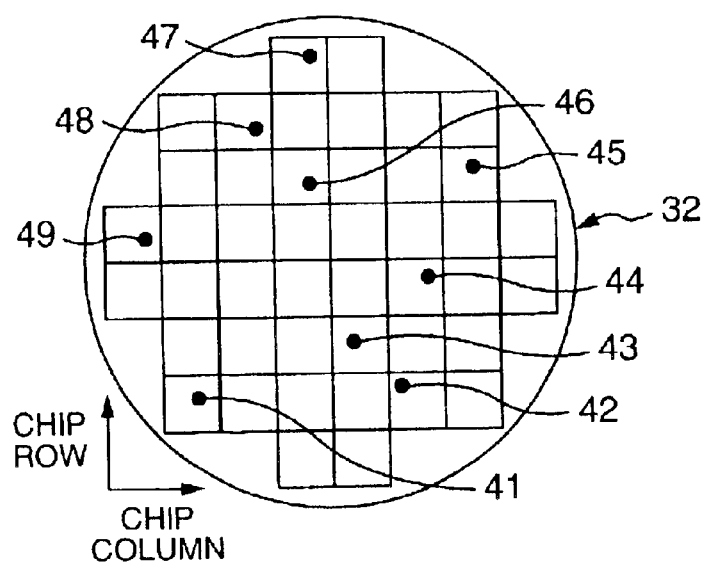
FIG. 2 shows an example of inspection data.
FIG. 3 shows an example of inspection data mapped on a wafer.

FIG. 2 shows an example of inspection data read at Step 11 shown in FIG. 1. Inspection data 31 is constituted of a product name, a lot number, a wafer number, an inspection process, a defect number, a chip column, a chip row, an intra-chip coordinate X, an intra-chip coordinate Y, and a defect size. In this example shown in FIG. 2, a defect inspection apparatus detects nine detection error candidates. In this example, although the unit of coordinate and size is nanometer, the unit is not limited only to nanometer.

FIG. 3 shows the inspection data 31 of FIG. 2 mapped on a wafer. A circle 32 represents a wafer, and a number of squares in the circuit 32 represent LSI chips. Solid black circles 41 to 49 correspond to the defect numbers "1" to "9" of the inspection data 31.

Figure 4:
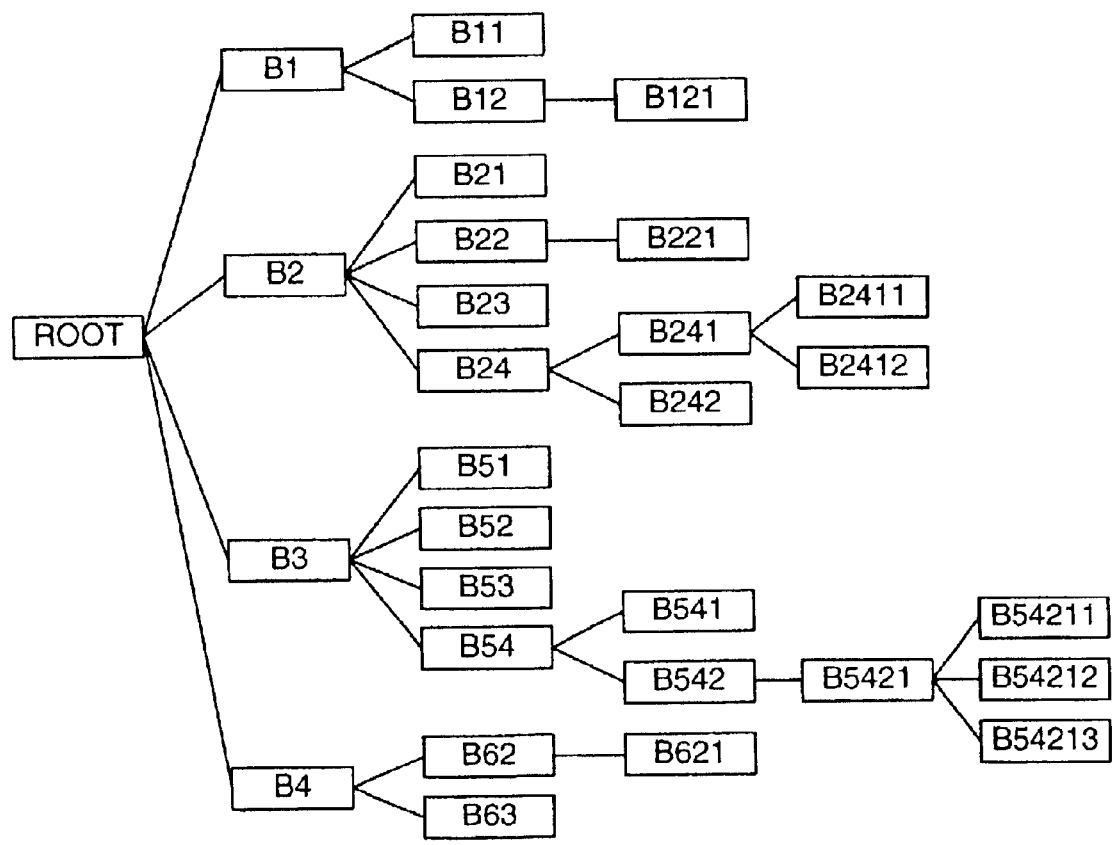
FIG. 4 shows an example of the structure of circuit layout information.

FIG. 4 shows an example of circuit layout information read at Step 2 of FIG. 1. FIG. 4 is a block diagram showing the computer-aided design (CAD) format for a circuit layout according to the semiconductor business standards. The circuit layout information is constituted of a tree structure starting from a root to branches representative of circuit functions. B1, B2, B3 and B4 represent different circuit blocks. The circuit block B1 has circuit blocks B11 and B12, and the circuit block B12 has a circuit block B121. The minimum unit of a circuit block is generally a combinational circuit and a sequential circuit. Generally, the circuit layout information is not structured in correspondence with each layer of a lamination structure of LSI, similar to the example shown in FIG. 4. The program of this invention can be executed also by using only the information of a layer corresponding to the inspection process described in the inspection data 31.

Figure 5:
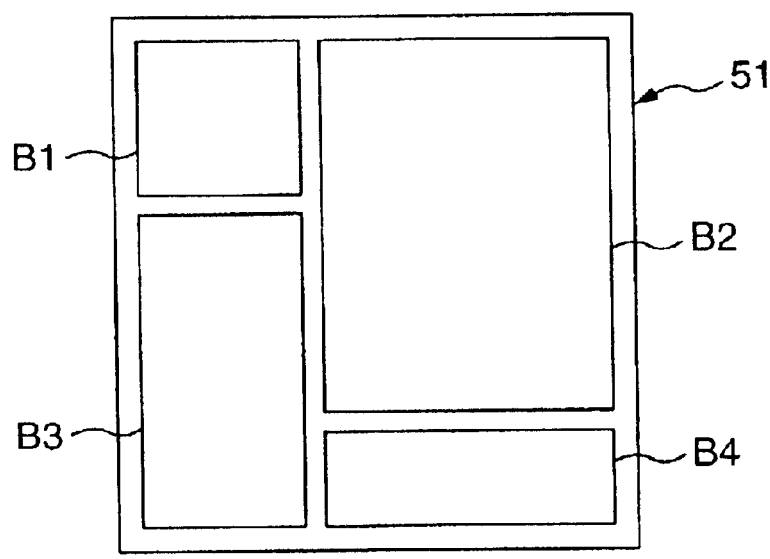
FIG. 5 is a plan view showing circuit blocks of the circuit layout information.

FIG. 5 is a plan view of an LSI chip having the circuit layout information B1, B2, B3 and B4 of FIG. 4. A square 51 represents a periphery of the LSI chip in which circuit blocks for B1, B2, B3 and B4 are formed. The area of the circuit block ROOT is the same as LSI periphery 51. Although not shown, the circuit blocks B1, B2, B3 and B4 have the branched circuit blocks shown FIG. 4 (B11, B12, B121 and the like).

Figure 6:
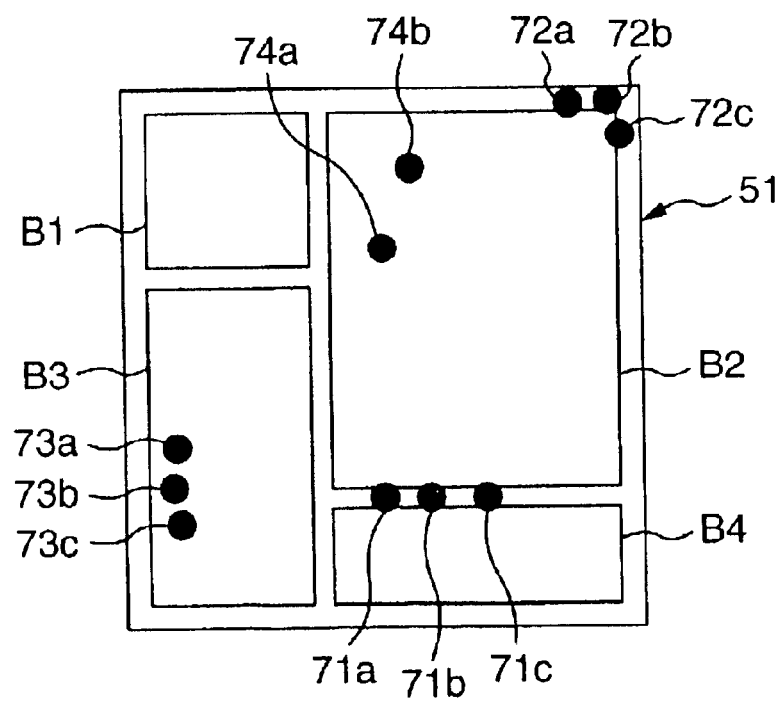
FIG. 6 is a plan view of circuit blocks of the circuit layout information, with the occurrence positions of detection errors being plotted.

An example of calculating the feature parameters from the inspection data and circuit layout at Step 16 in FIG. 1 will be described. FIG. 6 shows the check results of the occurrence positions of detection errors made by the present inventors by using past inspection data. FIG. 6 shows an example of the distribution of detection errors in an LSI chip output from a defect inspection apparatus. Data of detection errors in the circuit layout 51 of the LSI chip detected with a defect inspection apparatus is plotted in FIG. 6. A solid black circle represents each detection error. Detection errors 71a to 71c occurred in the boarder area between circuit blocks and each detection error had a different size. Detection errors 72a to 72c occurred in the peripheral area of the circuit block and each detection error had a different size. Detection errors 73a to 73c occurred in an area 10 micrometers inside the periphery of the circuit block and each detection error had a size equal to or smaller than 1 micrometer. Detection errors 74a and 74b occurred near the same circuit patterns, and each detection error had a size equal to or smaller than 1 micrometer and occurred in the circuit having a particular shape. It has been found from these findings that a detection error is much dependent upon the circuit layout and occurs in the boarder area between circuit blocks, in the peripheral area of a circuit block, in an area inside a particular circuit block and the like. It has also been found that detection errors of only a small size occur depending upon occurrence positions.

Figure 7:
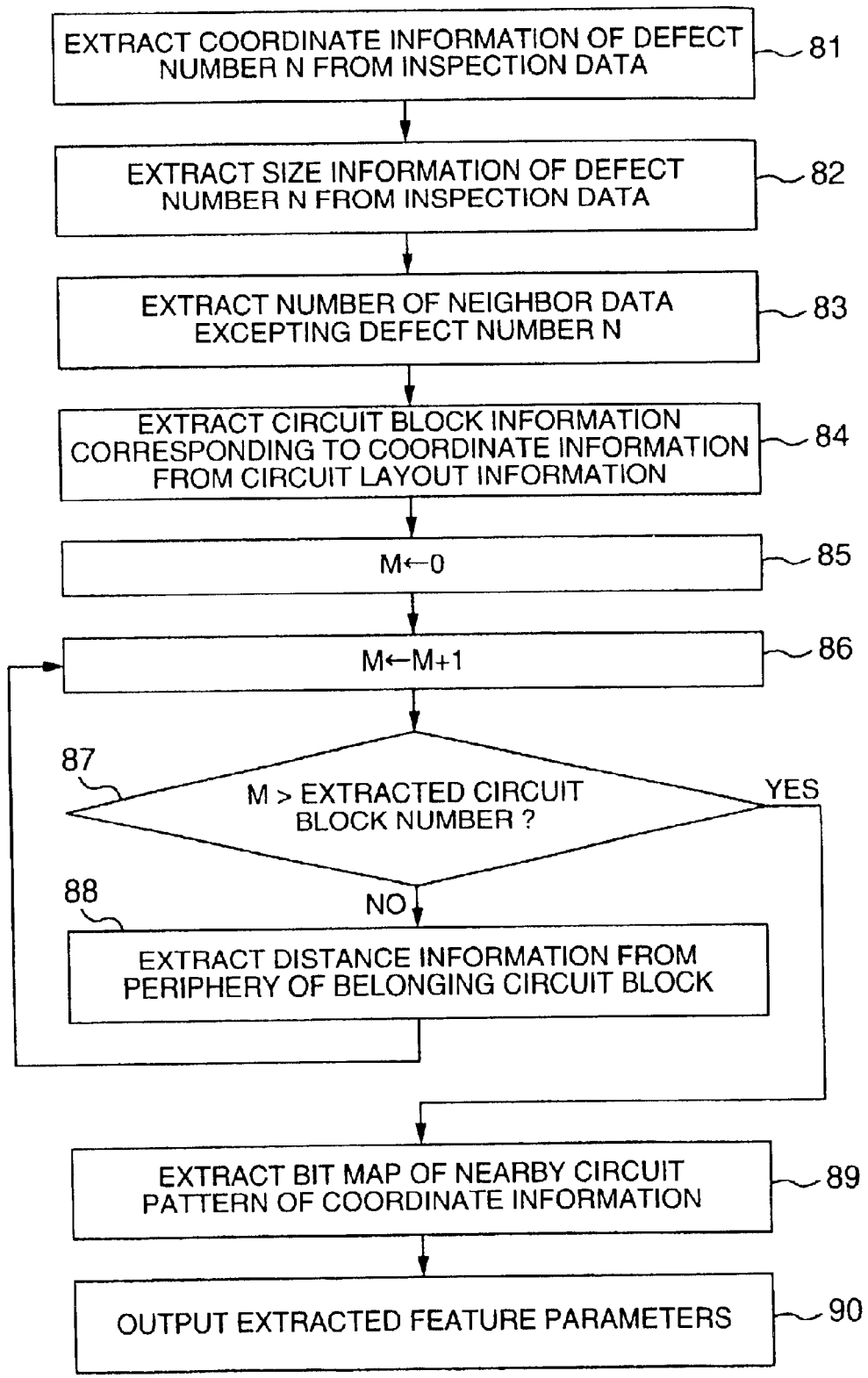
FIG. 7 is a flow chart illustrating an example of a process of extracting feature parameters from inspection data and circuit layout information, according to an embodiment of the invention.

FIG. 7 is a detailed flow chart illustrating an example of a process of calculating feature parameters from the relation between the inspection data and circuit layout at Step 16 in FIG. 1. First, at Step 81 coordinate information of a defect number N of inspection data is extracted, and at Step 82, size information is extracted. This data is herein assumed to be called a detection error candidate. Next, at Step 83 a distance between the coordinate position of the detection error candidate and the coordinate position of each defect number 1 to N−1, N+1 and etc. excepting the defect number N is calculated, and the number of defect numbers having a distance equal to or shorter than a predetermined threshold value is extracted as the number of neighbor data pieces. At Step 84 the circuit block information corresponding to the detection error candidate is extracted. For example, if the detection error candidate belongs to the circuit block B121 in the circuit block B1, the circuit block information of the circuit block ROOT, B1, B12 and B121 is extracted from the circuit layout information shown in FIG. 4. Next, at Step 85 "0" is substituted in a variable M, and at Step 86 the value of the variable M is incremented by "1". At Step 87 it is checked whether the number of circuit blocks extracted at Step 84 (e.g., if the detection error candidate belongs to the circuit block B121, the number of circuit blocks is "4") is larger than the value of the variable M, then the flow skips to Step 89, whereas if the value of the number of circuit blocks is equal to or smaller than the value of the variable M, then the flow advances to Step 88. At Step 88 a distance between the coordinate position of the detection error candidate and the periphery of each of the blocks to which the detection error candidate belongs (e.g., ROOT, B1, B12, B121) (for example, refer to FIG. 8) is calculated. The coordinate values of the detection error candidate in each circuit block can therefore be known. Namely, it can be known whether the detection error candidate is positioned in the boarder area between circuit blocks, whether the detection error candidate is positioned in the peripheral area of a circuit block, and etc. The known coordinate values are used as the data for determining at Step 17 whether the detection error candidate is a detection error. At Step 89 bit map data near the coordinate position of the detection error candidate is calculated and extracted from the circuit layout information (for example, refer to FIGS. 9 and 10). The circuit pattern near the detection error candidate can therefore be known. Namely, it can be known whether the circuit pattern near the detection error candidate is a special circuit. This is used as the data for determining at Step 17 whether the detection error candidate is a detection error. At Step 90 the extracted feature parameters (for example, refer to FIGS. 11 and 12) are output, for example, in the XML format to thereafter complete the execution of this process.

The process shown in FIG. 7 will be specifically described by using as an example the defect number "1" (i.e., N=1) in the inspection data shown in FIG. 2. First, at Step 81 X=5000000 and Y=7000000 are extracted as the coordinate values of the detection error candidate. At Step 82 1000 is extracted as the size of the detection error candidate. Next, at Step 83 if the predetermined threshold value for determining neighbor data is 200 micrometers, only the defect number "3" among the defect numbers "2" to "9" is extracted as the neighbor data so that the number of neighbor data pieces is "2" including the detection error candidate itself (defect number "1"). The distance between the coordinate positions of the detection error candidate and defect number "3" was 141 micrometers. At Step 84 assuming that the detection error candidate is the circuit block B21 in the circuit block B2 in the circuit block ROOT, the information of these three circuit blocks is extracted from the circuit layout information shown in FIG. 4. For example, the size of the circuit block ROOT is extracted as 10 mm in an X direction and 10 mm in a Y direction, and the size of the circuit block B2 is extracted as 6 mm in the X direction and 7 mm in the Y direction. Step 88 is executed for each of these three circuit blocks to calculate the position of the detection error candidate in each of the circuit block ROOT, circuit block B2 and circuit block B21 (calculate the distance between the detection error candidate and the periphery of each of the circuit blocks ROOT, B2 and B21).

Figure 8:
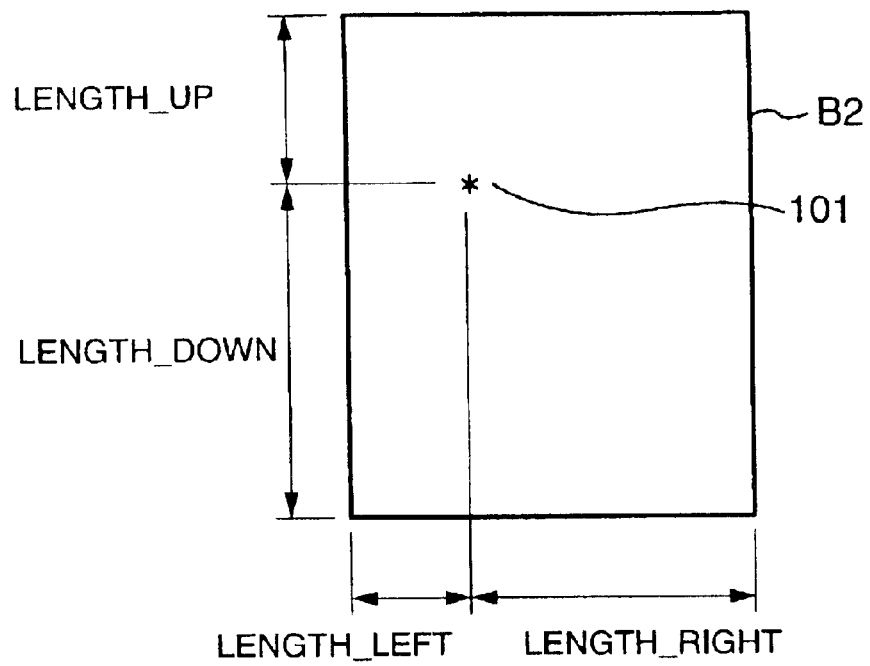
FIG. 8 shows an example of a method of defining a position of a detection error candidate in a circuit block.
Figure 9:
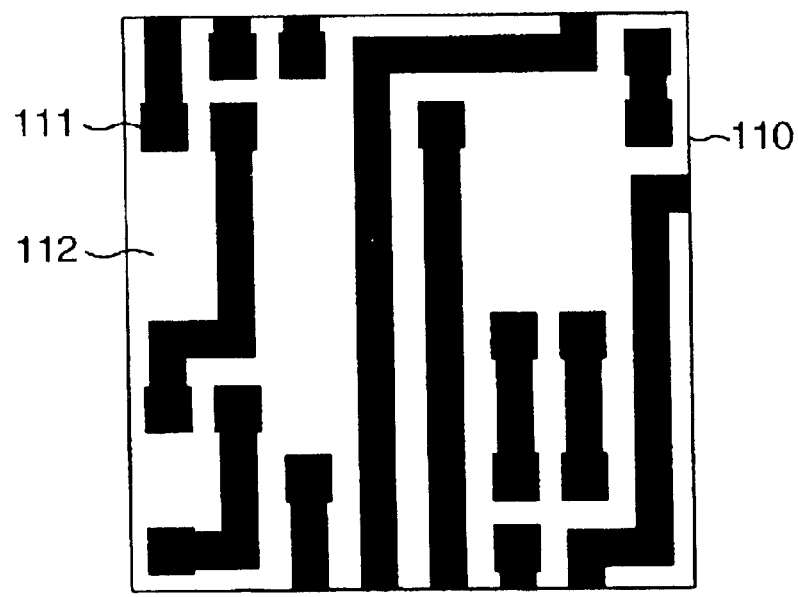
FIG. 9 shows an example of a circuit pattern near the detection error candidate.

FIG. 8 illustrates a calculation method by taking as an example the circuit block B2. An outer frame indicates the circuit block B2, and an asterisk mark 101 indicates the position of the detection error candidate in the circuit block B2. The distances between the center of the asterisk mark 101 and the outer frame are calculated as LENGTH_LEFT, LENGTH_RIGHT, LENGTH_UP and LENGTH_DOWN. An addition of LENGTH_LEFT and LENGTH_RIGHT corresponds to the length of the circuit block B2 in the X direction, and an addition of LENGTH_UP and LENGTH_DOWN corresponds to the length of the circuit block B2 in the Y direction. Next, at Step 89 bit map data of the circuit pattern near the coordinate position of the detection error candidate is extracted. FIG. 9 shows a circuit pattern 110 near the coordinate position of the detection error candidate, the circuit pattern 110 of 10 micrometers in the X and Y directions being enlarged. Black patterns 111 correspond to a circuit area (wiring area) and white patterns correspond to an area other than the circuit area. FIG. 10 is binary bit map data 113 which is constituted of a matrix of 0s and 1s partitioned with commas having twenty rows and twenty columns. A bit "1" corresponds to the circuit area, and a bit "0" corresponds to other areas. In this example, although the matrix of twenty columns and twenty rows is used because of the drawing size, a matrix having more columns and rows may be used to draw a more detailed circuit pattern.

After these Steps are executed, at Step 90 the feature parameters extracted at Steps 81 to 89 are output which are shown in FIGS. 11 and 12. FIGS. 11 and 12 show one continuous XML data set although it is shown divisionally because of the drawing size. FIGS. 11 and 12 show the feature parameters of the defect number "1" in the inspection data 31. As an OBJECT tag, a product name is written in a PRODUCT tag, a lot number is written in a LOT tag, a wafer number is written in a WAFER tag, a layer name of an LSI lamination structure subjected to the defect inspection is written in a LAYER tag. A DETECTION tag and a LAYOUT tag show the feature parameters of the defect number "1". Written in the DETECTION tag are the coordinate values X and Y of the detection error candidate extracted at Step 81, the size of the detection error candidate extracted at Step 82, and the threshold value and the number of neighbor data pieces extracted at Step 83. Written in the LAYOUT tag are the circuit block information and bit map data of an area around the coordinate position of the detection error candidate extracted at Steps 84 to 89. Written in a CIRCUIT_BLOCK tag in the LAYOUT tag are the circuit block name and the position (LENGTH_LEFT, LENGTH_RIGHT, LENGTH_UP and LENGTH_DOWN) of the detection error candidate in each extracted circuit block. Written in a CIRCUIT_PATTERN tag are the circuit pattern range (size), the number of divisions (the number of bits of data shown in FIG. 10 (resolution)) and the bit map data itself which were extracted from the circuit layout information shown in FIG. 4 as the circuit block name at the branch end (the end of the tree shown in FIG. 4, i.e., the right end of the tree) and bit map data.

Next, a matching process of comparing the feature parameters (criterion information for detection error determination) in the detection error database with the feature parameters (information) extracted at Step 16 shown in FIG. 1 will be described in detail, the matching process of this embodiment being executed at Step S17.

FIGS. 13 and 14 show examples of feature parameter data (detection error determination condition data) in the detection error database. The detection error database is created by using feature parameter data including detection errors in past inspection data output from a defect inspection apparatus and its circuit layout information. If feature parameter data same as or similar to the feature parameter data registered in the detection error database is extracted from the inspection data such as shown in FIGS. 11 and 12, the detection error candidate is determined as a detection error.

FIG. 13 shows an example of the detection error database storing bit map data near the coordinate position of a past detection error. The conditions are written in a RULE tag. The inspection data has a product name of a character string starting from ASIC3 and a layer name of METAL1. The registered bit map data has an X direction size of 10 micrometers (10000 nanometers) and a Y direction size of 10 micrometers (10000 nanometers) in a matrix shape of 20×20. The bit map data is written in a BITMAP tag. By using this bit map data as a template, the data of the detection error candidate output at Step 90 shown in FIG. 7 is subjected to the matching process. This detection error database describes that two bits are shifted in the X and Y direction in the matching process and that if the matching rate is in the range from 90% to 100% (in the same or similar range of the feature parameters of the circuit pattern), the detection error candidate is determined as a detection error. For example, in the matching process between the feature parameters in the detection error database and the feature parameters of the detection error candidate shown in FIGS. 11 and 12, if the bit map shown in FIG. 13 is shifted to the left by one bit, the matching rate becomes 100% (same circuit pattern feature parameters).

FIG. 14 shows an example of the detection error database registering the circuit block in which a detection error occurred and the position of the past detection error in the circuit block. Similar to FIG. 13, the inspection data has a product name of a character string starting from ASIC3 and a layer name of METAL1. This detection error database describes that as the conditions of determining the detection error candidate data as a detection error, the size is required to be 0 to 2 micrometers (2000 nanometers) and two or more neighbor data pieces including the detection error candidate data exists in an area equal to or shorter than 200 micrometers. In addition, if the detection error candidate data exists in an area of ±20 micrometers in the X direction and ±10 micrometers in the Y direction around the position in the circuit block B2 at the LENGTH_LEFT of 3 mm and LENGTH_UP of 1 mm, the detection error candidate is determined as a detection error.

FIG. 15 shows an example of the inspection data with the detection error determination results output at Step 19 shown in FIG. 1. In output data 33, a detection determination flag is added to the inspection data 31. The inspection data with "1" in the detection error column was determined as a detection error. In this example, the defect numbers "1" and "3" were determined as a detection error.

As described above, a detection error is determined by using the inspection data detected with the defect inspection apparatus and the detection error database.

As the information for determining a detection error, it is possible to use at least one information piece of the distance between the coordinate position of the detection error candidate extracted at Step 88 and the bit map data of the circuit pattern near the coordinate position of the detection error candidate extracted at Step 89.

The detection error determining method is not limited only to the matching process between the feature parameter data of a detection error candidate and the feature parameter data (detection error determining condition data) registered in the detection error database, but other methods may be used for determining a detection error. For example, defect data of the inspection data such as shown in FIGS. 11 and 12 is collected for each defect, and if the defect data of each defect whose feature parameters are in the same or similar range exceeds a predetermined threshold value (e.g., ten or more defect data pieces, 50% or higher or the like), the detection error candidate may be determined as a detection error.

Next, an example of a method of creating the detection error database of the invention will be described.

Figure 16:
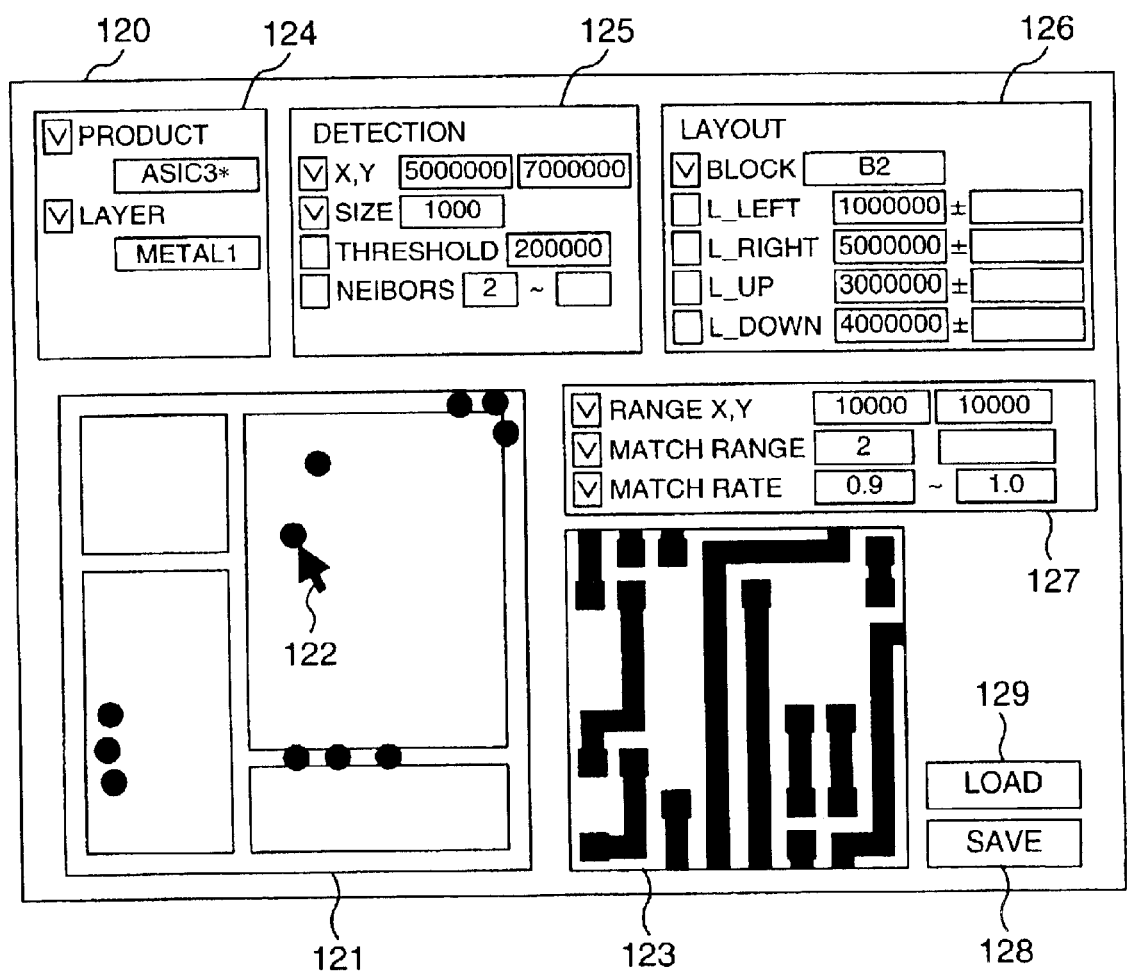
FIG. 16 shows an example of a graphical user interface for creating the detection error database.

FIG. 16 shows an example of a graphical user interface (GUI) for creating the detection error database. A screen 120 displays a circuit layout 121 of an LSI chip, and occurrence positions of past detection errors are plotted in the circuit layout 121. The detection error was determined by using a review tool. Each plotted detection error can be clicked with a mouse 122 so that the clicked detection error and its circuit layout are displayed. For example, an information window 124 displays the product name of LSI and a layer name to be inspected. An information window 125 displays the coordinate values of a detection error in the chip, the size of the detection error, the threshold value for neighbor data determination, the number of neighbor data pieces and the like. An information window 126 displays a circuit block name, the position of the detection error in the circuit block, a circuit pattern 123 near the detection error and the like. The display area of the circuit pattern 123 is designated in an information window 127. The conditions to be registered in the detection error database for the selected detection error are determined by inputting or editing data displayed in the information windows 124 to 127. Data with a V mark (check mark) is registered when a SAVE button 128 is clicked. Data without the V mark is not registered. The data once registered by the SAVE button 128 can be read and edited again by clicking a LOAD button 129. For example, the threshold value may be set again to perform the detection error determination again. In the example shown in FIG. 16, the detection error database shown in FIG. 13 is created. Therefore, although PRODUCT in the information window 124 uses the product name such as ASIC3100 to read the detection error data, the product name is edited as ASIC3*. In addition, the V mark is not added to the threshold value for neighbor data determination and the number of neighbor data pieces in the information window 125 to make them unnecessary. Similarly, the detection error position in the circuit block in the information window 126 is made to be unnecessary data. In order to register the circuit pattern 123, the V mark is added to the shift range of matching and the matching rate in the information window 127 to input them. As the SAVE button 128 is clicked in this state, data shown in FIG. 13 is created and registered in the detection error database.

Next, an example of a hardware structure for executing the program of the invention will be described. Examples of an inspection system and an inspection apparatus are given.

Figure 17:
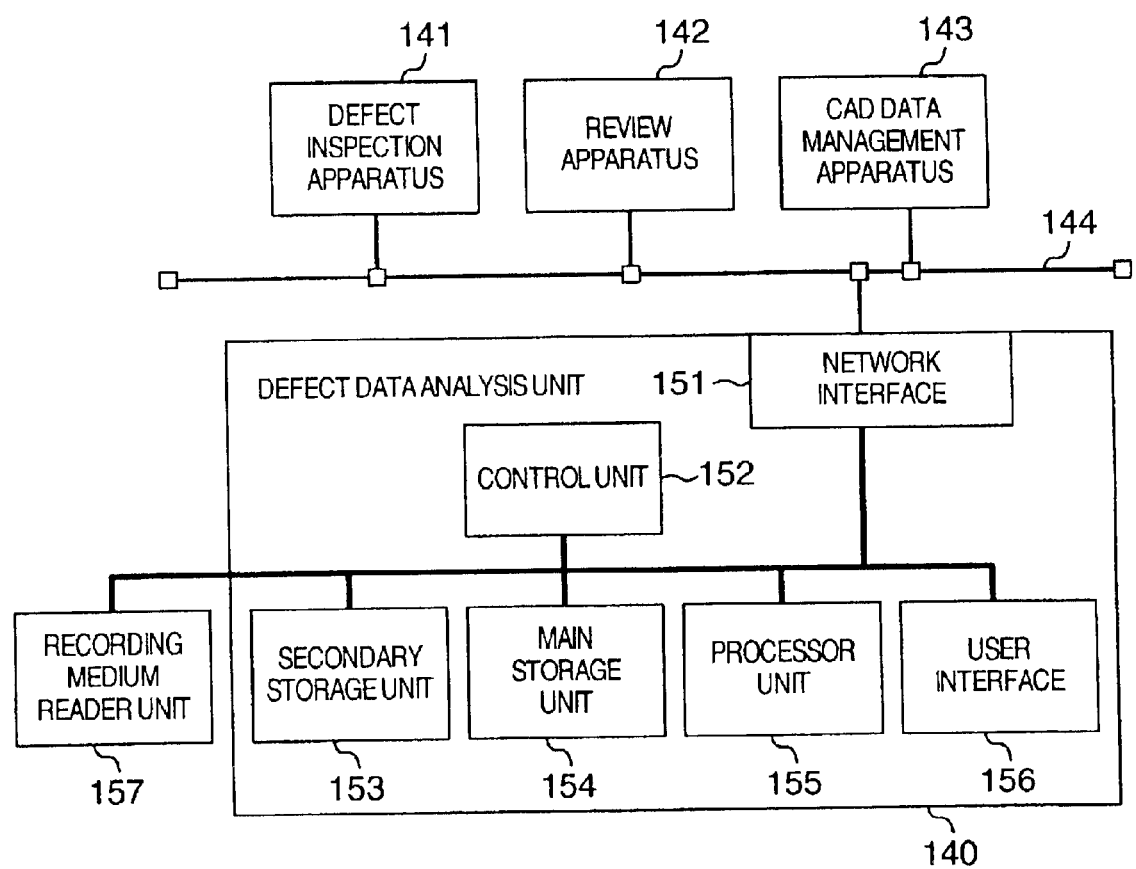
FIG. 17 shows an example of an inspection system applying the program of the invention to a general personal computer.

FIG. 17 shows an example of the inspection system. A defect data analysis unit 140, a defect inspection apparatus 141, a review apparatus 142 and a CAD data management apparatus 143 are interconnected by a local area network (LAN) 144. The defect data analysis unit 140 has a network interface 151, a control unit 152, a secondary storage unit 153, a main storage unit 154, a processor unit 155 and a user interface 156. The defect data analysis unit 140 may be a general personal computer. Inspection data 31 shown in FIG. 2 is transferred from the defect inspection apparatus 141 to the defect data analysis unit 140. An inspection data reception program stored beforehand in the secondary storage unit 153 is read into the main storage unit 154 and executed by the processor unit 155. The inspection data 31 is therefore stored in the secondary storage unit 153 via the network interface 151. The circuit layout information shown in FIG. 4 is transferred from the CAD data management apparatus 143 to the defect data analysis unit 140. A circuit layout information reception program stored beforehand in the secondary storage unit 153 is read into the main storage unit 154 and executed by the processor unit 155. The circuit layout information is therefore stored in the secondary storage unit 153 via the network interface 151. The program of the invention is stored beforehand in the secondary storage unit 153. The program of the invention may be downloaded into the secondary storage unit 153 from LAN 144 via the network interface 151, or a recording medium reader unit 157 may read a recording medium (e.g., CD-ROM, DVD and the like) storing the program of the invention and stores the program in the secondary storage unit 153. This program is read from the secondary storage unit 153 into the main storage unit 154 to execute the process shown in FIG. 1. In this process, at Steps 11 and 12 the inspection data 31 and circuit layout information are read from the secondary storage unit 153 into the main storage unit 154. In the process shown in FIG. 1, at Step 19 the inspection data 33 shown in FIG. 15 is stored in the secondary storage unit 153 to thereafter stop the program. The detection error database shown in FIGS. 13 and 14 are stored in the secondary storage unit 153. Creating the detection error database illustrated in FIG. 16 is performed by using a display of the user interface 156. If the defect data analysis program described in JP-A-10-115594 and the like is stored in the secondary storage unit 153 and executed by using the inspection data 33 after the detection error determination, the manufacture yield of LSI can be effectively improved. Similarly, it is effective if a defect of the inspection data not determined as a detection error is analyzed with the review apparatus 142 by using the inspection data 33 after the detection error determination.

Figure 18:
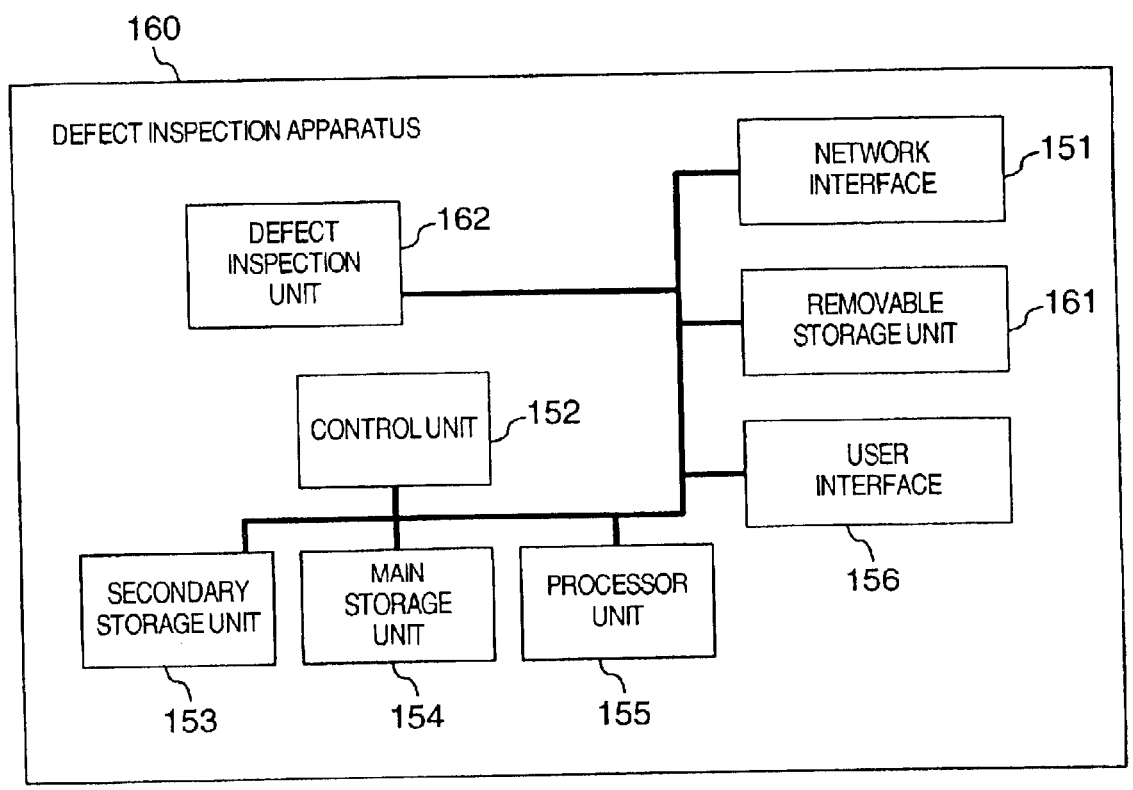
FIG. 18 shows an example of a defect inspection apparatus to which the program of the invention is applied.

FIG. 18 shows an example of the defect inspection apparatus. Similar to the defect data analyzing unit shown in FIG. 17, a defect inspection apparatus 160 has a network interface 151, a control unit 152, a secondary storage unit 153, a main storage unit 154, a processor unit 155 and a user interface 156, and in addition a removable storage unit 161 and a defect inspection unit 162. The removable storage unit 161 may be a compact disc, an optical disc or the like and stores data of a large capacity such as circuit layout information. The defect inspection unit 162 can inspect a defect by using an illumination/image detector unit, an XY stage and the like. Defect inspection is made by the defect inspection unit 162, and the detected inspection data 31 is stored in the secondary storage unit 153. The circuit layout information may be input from the network interface 151 via LAN and stored in the secondary storage unit 153, or the removable storage unit 161 may be used to store the circuit layout information in the secondary storage unit 153. The program of the invention is executed in the manner similar to the inspection system shown in FIG. 17. The program of the invention is stored beforehand in the secondary storage unit 153. The program of the invention may be read from a recording medium (e.g., CD-ROM, DVD and the like) into the removable storage unit 161 and then stored in the secondary storage unit 153.

In this invention, whether each of the particles or pattern defects of the inspection data to be inspected is a detection error or not may be determined at Step S18 shown in FIG. 1 by extracting at Step 16 the information indicating the relation between at least one information piece of the coordinate value information and size information of each of the particles or pattern defects of the inspection data input at inspection data input Step and the drawing information input at drawing information input Step, and by comparing at Step 17 the information extracted at information extracting Step with the determination criterion information registered in advance.

As described so far, the program of the invention is executed by using the inspection system and the processor unit and main storage unit in the inspection apparatus and determines a detection error from the inspection data detected with the defect inspection apparatus. The detection error determination results are utilized for the detailed analysis of a detection error so that the manufacture yield of LSI can be improved.

According to the invention, by using the past detection error data and the circuit layout information corresponding to the detection error data, the detection error database is created. It is therefore possible to efficiently find a detection error from inspection data newly output from the defect inspection apparatus. By utilizing the inspection data excluding detection errors for the defect analysis, the manufacture yield of electronic devices typically semiconductor integrated circuits can be improved effectively.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. An inspection data analyzing program to be executed on hardware for determining a detection error from output data of an inspection apparatus which detects a particle or a pattern defect of a circuit pattern, the inspection data analyzing program comprising:

reading inspection data output from the inspection apparatus, wherein the inspection data output includes at least one information piece of coordinate value information and size information of the particle or pattern defect of the circuit pattern;

reading drawing data of a product of the circuit pattern;

extracting information representative of a relation between at least one information piece of coordinated value information and size information of the particle or pattern defect of the circuit pattern in the inspection data output and the drawing data;

obtaining information representing a relation between detection error data obtained based on past inspection data output as to a circuit pattern from output data of the inspection apparatus and circuit layout data of a computer-aid design (CAD) and storing the information thus obtained as a detection error database;

comparing the information extracted with detection error database to determine whether each particle or pattern defect of the circuit pattern in the inspection data is a detection error; and subjecting newly output inspection data excluding detection error data thus determined to defect analysis.

2. An inspection data analyzing program according to claim 1, wherein the drawing data read is circuit layout data generated by computer-aided design (CAD).

3. An inspection data analyzing program according to claim 1, wherein the information extracted includes coordinate value information of each particle or pattern defect of the circuit pattern in the inspection data in a circuit block corresponding to the drawing data.

4. An inspection data analyzing program according to claim 1, wherein the information extracted includes size information of each particle or pattern defect of the circuit pattern in the inspection data.

5. An inspection data analyzing program according to claim 1, wherein the information extracted includes a circuit pattern near each particle or pattern defect of the circuit pattern in the inspection data.

6. An inspection data analyzing program according to claim 1, wherein the database is data representative of occurrence positions of past detection errors in a circuit block in the drawing data.

7. An inspection system for determining a detection error from output data of an inspection apparatus which detects a particle or a pattern defect of a circuit pattern, comprising:

an inspection apparatus for detecting and outputting a particle or a pattern detect of a circuit pattern;

a drawing data managing apparatus for storing drawing data of a product of the circuit pattern; and a defect data analyzing unit connected to said inspection apparatus and said drawing data managing apparatus, via a network, wherein said defect data analyzing unit comprises:

an input unit for collecting inspection data detected with said inspection apparatus and containing at least one information piece of coordinate value information and size information of each particle or each pattern defect of the circuit pattern and the drawing data managed by said drawing data managing apparatus;

a storage unit for storing the inspection data, the drawing data, and information representing a relation between detection error data obtained based on past inspection data as to a circuit pattern from output data of said inspection apparatus and circuit layout data of a computer-aid design (CAD) as a detection error database;

an information extracting unit for extracting information representative of a relation between at least one piece of coordinate value information and size information of each particle or each pattern defect of the circuit pattern in the inspection data stored in said storage unit and the drawing data;

a detection error determining unit for comparing the information extracted by said information extracting unit with the detection error database stored beforehand in said storage unit to determine whether each particle or each pattern defect of the circuit pattern in the inspection data is a detection error; and an analysis unit for subjecting the information extracted by said information extracting unit excluding detection error data thus determined to defect analysis.

8. An inspection apparatus for determining a detection error from output data of an inspection apparatus which detects a particle or a pattern defect of a circuit pattern, comprising:

a defect inspecting unit for detecting a particle or a pattern detect of a circuit pattern;

an input unit for inputting drawing data of a product of the circuit pattern;

a storage unit for storing inspection data detected with said defect inspecting unit and containing at least one information piece of coordinate value information and size information of each particle or each pattern defect of the circuit pattern, the drawing data input by said input unit, and information representing a relation between detection error data obtained based on past inspection data as to a circuit pattern from output data of the inspection apparatus and circuit layout data of a computer-aid design (CAD) as a detection error database;

an information extracting unit for extracting information representative of a relation between at least one information piece of coordinate value information and size information of each particle or each pattern defect of the circuit pattern in the inspection data stored in said storage unit and the drawing data; and a detection error determining unit for comparing the information extracted by said information extracting unit with the detection error database stored beforehand in said storage unit to determine whether each particle or each pattern defect of the inspected object in the inspection data is a detection error; and an analysis unit for subjecting the information extracted by said information extracting unit excluding detection error data thus determined to defect analysis.

9. An inspection data analyzing method of determining a detection error from output data of an inspection apparatus which detects a particle or a pattern defect of a circuit pattern, the inspection data analyzing method comprising:

reading inspection data output from the inspection apparatus, including at least one information piece of coordinate value information and size information of the particle or pattern defect of the circuit pattern;

reading drawing data of a product of the circuit pattern;

extracting information representative of a relation between at least one information piece of coordinated value information and size information of the particle or pattern defect of the circuit pattern in the inspection data and the drawing data;

obtaining information representing a relation between detection error data obtained based on past inspection data as to a circuit pattern from output data of the inspection apparatus and circuit layout data of a computer-aid design (CAD) and storing the information thus obtained as a detection error database;

comparing the information extracted with the detection error database to determine whether each particle or pattern defect of the circuit pattern in the inspection data is a detection error; and subjecting newly output inspection data excluding detection error data thus determined to defect analysis.

10. An inspection data analyzing method according to claim 9, wherein the drawing data read is circuit layout data generated by the computer-aided design (CAD).

11. An inspection data analyzing method according to claim 9, wherein the information extracted includes coordinate value information of each particle or pattern defect of the circuit pattern in the inspection data in a circuit block corresponding to the drawing data.

12. An inspection data analyzing method according to claim 9, wherein the information extracted includes size information of each particle or pattern defect of the circuit pattern in the inspection data.

13. An inspection data analyzing method according to claim 9, wherein the information extracted includes a circuit pattern near each particle or pattern defect of the circuit pattern in the inspection data.

14. An inspection data analyzing method according to claim 9, wherein the database is data representative of occurrence positions of past detection errors in a circuit block in the drawing data.

15. An inspection data analyzing method of determining a detection error from output data of an inspection apparatus which detects a particle or a pattern defect of a circuit pattern, the inspection data analyzing method comprising the steps of:

obtaining information representing a relation between detection error data obtained based on past inspection data as to a circuit pattern from output data of the inspection apparatus and circuit layout data of a computer-aid design (CAD) and storing the information thus obtained as a detection error database;

comparing inspection data as to a circuit pattern to be inspected output from the inspection apparatus with the information stored in the detection error database to determine whether the output inspection data as to the circuit pattern to be inspected is detection error data as to each particle or pattern defect of the circuit pattern to be inspected; and subjecting the output inspection data excluding detection error data thus determined to defect analysis.

16. An inspection data analyzing program to be executed on hardware for determining a detection error from output data of an inspection apparatus which detects a particle or a pattern defect of a circuit pattern, the inspection data analyzing program comprising:

obtaining information representing a relation between detection error data obtained based on past inspection data as to a circuit pattern from output data of the inspection apparatus and a circuit layout data of a computer-aid design (CAD) and storing the information thus obtained as a detection error database;

comparing inspection data as to a circuit pattern to be inspected output from the inspection apparatus with the information stored in the detection error database to determine whether output inspection data as to the circuit pattern to be inspected is detection error data as to each particle or pattern defect of the circuit pattern to be inspected; and subjecting the newly output inspection data excluding detection error data thus determined to defect analysis.

17. An inspection system for determining a detection error from output data of an inspection apparatus which detects a particle or a pattern defect of a circuit pattern, the inspection apparatus comprising:

a storage unit which stores, as a detection error database, information representing a relation between detection error data obtained based on past inspection data as to a circuit pattern from output data of the inspection apparatus and circuit layout data of a computer-aid design (CAD);

a detection error determining unit which compares inspection data output from the inspection apparatus with data stored in the detection error database to determine whether output inspection data is detection error data as to each particle or pattern defect of the circuit pattern thus detected; and an analyzing unit which subjects the output inspection data excluding detection error data thus determined to defect analysis.

* * * * *